United States Patent [19]

Frigerio et al.

[11] Patent Number: 5,449,520
[45] Date of Patent: Sep. 12, 1995

[54] PHARMACEUTICAL COMPOSITION FOR RECTAL ADMINISTRATION OF ACTIVE PRINCIPLES EXHIBITING A PREVALENTLY TOPICAL MEDICATION ACTION AT THE COLON LEVEL

[75] Inventors: Giuliano Frigerio, Arese; Enzo Giorgetti, Milan; Emilia Chiodini, Marcallo con Casone, all of Italy

[73] Assignee: Giuliani S.p.A., Milan, Italy

[21] Appl. No.: 130,624

[22] Filed: Oct. 1, 1993

Related U.S. Application Data

[63] Continuation of Ser. No. 714,207, Jun. 12, 1991, abandoned.

[30] Foreign Application Priority Data

Jul. 27, 1990 [IT] Italy ................................. 21104/90

[51] Int. Cl.$^6$ ............................................. A61F 9/02
[52] U.S. Cl. ................................. 424/436; 424/444
[58] Field of Search ............... 424/436, 485; 514/16, 514/682

[56] References Cited

U.S. PATENT DOCUMENTS

| | | | |
|---|---|---|---|
| 4,609,403 | 9/1986 | Wittwer et al. | 106/122 |
| 4,670,419 | 6/1987 | Uda et al. | 514/16 |
| 4,814,183 | 3/1989 | Zentner | 424/485 |
| 5,310,762 | 5/1994 | Latter et al. | 514/682 |

*Primary Examiner*—Thurman K. Page
*Assistant Examiner*—William E. Benston, Jr.
*Attorney, Agent, or Firm*—Hedman, Gibson & Costigan

[57] ABSTRACT

The invention provides a pharmaceutical composition for the rectal administration of active principles which exhibit a prevalently topical medication action at the colon level, characterized in that said active principles are formulated in a fluid vehicle able to generate a foam on rectal administration.

11 Claims, No Drawings

PHARMACEUTICAL COMPOSITION FOR RECTAL ADMINISTRATION OF ACTIVE PRINCIPLES EXHIBITING A PREVALENTLY TOPICAL MEDICATION ACTION AT THE COLON LEVEL

This is a continuation of application Ser. No. 07/714,207, filed Jun. 12, 1991 which is now abandoned.

This invention relates to the administration of agents which are pharmacologically active against intestinal disturbances, and provides a pharmaceutical composition which can be administered rectally for this purpose. It is of particular but not exclusive application in the administration of 5-amino-salicylic acid (hereinafter known as 5-ASA or mesalazine) for treating disturbances of the colon and rectum.

The present invention is directed generally to any active principle exhibiting a prevalently topical medication action on various levels of the colon.

Particularly but not exclusively it is directed towards medicaments with an antiinfective/antibiotic, antiinflammatory/antiphlogistic, antispastic, antimeteoric, prokinetic or laxative action.

It is known that in treating affections or disturbances of the colon or rectum, topical administration of the pharmacologically active agent can be used, as it rapidly reaches and acts on the point at which the disturbance is located.

In the known art, such pharmacologically active agents can be administered rectally using suppositories or enemas. However, rectal administration using suppositories is generally unable to act beyond the rectal tract, whereas an enema is generally rarely able to pass beyond the left side of the colon.

For the purposes of the present invention the ability of the active principles in question to retrodiffuse, ie achieve a retrograde progression as extended as possible from the point of administration along the colon and provide uniform distribution of such active principles, is very important.

In this regard, it is known that a 5-ASA enema (4 g in 100 ml) has appreciable retrodiffusion as far as the splenic flexure of the colon, and is therefore suitable for curing patients suffering for example from sinistral ulcerous colitis, ie a distal disease extending as far as the splenic flexure. However this enema does not normally have the capacity to retrodiffuse beyond the left side of the colon. In addition, an enema generally suffers from the serious problem of a low and often insufficient ability to persist by adhesion to the intestinal walls, and a lack of distribution uniformity, thus reducing the capacity of the active principle to act in the tract which it reaches.

In this respect, according to the objects of the invention the active principle in question should not only have high retrodiffusion but should also exhibit an effective persistent and uniform action in those tracts of the colon which it succeeds in reaching.

Preferably, this activity should be maintained even after intestinal evacuation by the subject treated.

The active principles for medication at the colon level towards which the present invention is directed are not necessarily limited with regard to the type of therapeutic action. What they must generally possess is prevalently topical action and exhibit low systemic absorption, with high general toleration even if a certain level of systemic absorption does exist.

According to the present invention it has now been surprisingly found that the aforesaid objects are attained by a pharmaceutical composition for the rectal administration of active principles which exhibit a prevalently topical medication action at the colon level, characterised in that said active principles are formulated in a fluid vehicle able to generate a foam on rectal administration.

The compositions of the present invention are pharmaceutical preparations composed in such a manner as to be able to rectally introduce medicaments of prevalently topical action which are vehicled in more or less consistent foam, and generally active at high concentrations (5–50%).

According to the invention, the foam must be generated at or close to the moment of therapeutical application. Hence the known formulation and dispensing technology applicable to foam cans used for example in cosmetics is therefore suitable. Here, the active principle is vehicled in the liquid state with at least one propellant and a surfactant with foaming action.

At the moment of use the dispensing valve of the can allows rapid expansion of the propellant, which triggers and enhances the foaming action of the surfactant, which thus emerges to entrain the medicated liquid in the form of foam.

The propellant expansion energy is absorbed mainly in forming the foam, thus allowing rectal application without risk.

The liquid vehicle must be water-based or more rarely based on highly hydrophilic organic substances to allow the surfactant to perform its foaming action, which however must not be inhibited by the other substances present in the formulation, such as the active principles and their stabilizers, whereas the specific adjuvants (such as foam consistency correctors) must be chosen from those with strong hydrophilic and lipophilic characteristics. In administering such compositions, it is sufficient to obtain foams of medium consistency, with a minimum volume of 100 ml of foam introduced into the rectum.

In general, according to the invention a composition comprises generally any substances possessing prevalently topical pharmacological activity towards the distal intestinal tract as active principles; suspending substances, solubilizers, preservatives etc. as active principle adjuvants; water or highly hydrophilic organic liquids (such as propyleneglycol, polyethyleneglycol) as fluid vehicle; high HLB (hydrolipophilic index) surfactants, non-ionic surfactants (such as polysorbates), anionic surfactants (such as sodium laurylsulphate), or cationic surfactants (such as benzalkonium chloride) as foaming surfactants; medium HLB surfactants (such as polyoxyethyleneglycol isostearate) or typical cream emulsion thickeners (such as cetyl alcohol, propyleneglycol) as foam thickeners; freon (such as freon 12, freon 114) as propellants; hydrocarbons (such as isobutane, N-butane or propane); and miscellaneous substances (such as $CO_2N$).

The active principle is solubilized or suspended in a suitable liquid vehicle containing a foaming surfactant. The liquid is placed in an atomizer can sealed by a dispensing valve and then pressurized by feeding a suitable quantity of propellant through the valve.

The following examples of the invention are given as non-limiting illustration only. In these examples the various ingredients of each composition are assigned a successive number (from 01 upwards) for greater ease of description.

EXAMPLE 1

| RECTAL FOAM 10% MESALAZINE | |
|---|---|
| % COMPOSITION (of foam or pressurized liquid) | |
| 01 Mesalazine (active principle) | 10 |
| 02 Xanthan gum (active principle thickener and suspender) | 0.2 |
| 03 Potassium metabisulphite (active principle antioxidant) | 0.25 |
| 04 EDTA bisodium salt (active principle antioxidant) | 0.3 |
| 05 Sodium benzoate (antibacterial-antimildew agent) | 0.38 |
| 06 Polysorbate 20 (foaming surfactant) | 4 |
| 07 Polyglycol 300 isostearate (foam thickener) | 4 |
| 08 Purified water | 70.87 |
| 09 Freon 12 (propellant) | 6.5 |
| 10 Freon 114 (propellant) | 3.5 |

Preparation method:

A) The components 03, 04, 05 and 02 are dissolved in 08 in the stated order in a stainless steel dissolving vessel of suitable capacity fitted with a propeller stirrer and turboemulsifier.

B) 06, 07 and finally 01 are added while stirring, and the turboemulsifier is then operated for 15 minutes.

C) Using a metering pump, the suspension is metered in the volume corresponding to the theoretical weight into aerosol cans while stirring.

D) Each can is immediately sealed by clinching the dispenser valve and is then pressurized by means of the propellant, which is fed in under pressure in a suitable quantity by a pumping device.

EXAMPLE 2

| RECTAL FOAM 20% MESALAZINE | |
|---|---|
| % COMPOSITION (of foam or pressurized liquid) | |
| 01 Mesalazine (active principle) | 20 |
| 02 Xanthan gum (active principle thickener and suspender) | 0.2 |
| 03 Potassium metabisulphite (active principle antioxidant) | 0.25 |
| 04 EDTA bisodium salt (active principle antioxidant) | 0.3 |
| 05 Sodium benzoate (antibacterial-antimildew agent) | 0.38 |
| 06 Polysorbate 20 (foaming surfactant) | 4 |
| 07 Polyglycol 300 isostearate (foam thickener) | 4 |
| 08 Purified water | 60.87 |
| 09 Freon 12 (propellant) | 6.5 |
| 10 Freon 114 (propellant) | 3.5 |

Preparation method:

A) The components 03, 04, 05 and 02 are dissolved in 08 in the stated order in a stainless steel dissolving vessel of suitable capacity fitted with a propeller stirrer and turboemulsifier.

B) 06, 07 and finally 01 are added while stirring, and the turboemulsifier is then operated for 15 minutes.

C) Using a metering pump, the suspension is metered in the volume corresponding to the theoretical weight into aerosol cans while stirring.

D) Each can is immediately sealed by clinching the dispenser valve and is then pressurized by means of the propellant, which is fed in under pressure in a suitable quantity by a pumping device.

EXAMPLE 3

| RECTAL FOAM 5% PEPPERMINT | |
|---|---|
| % COMPOSITION (of foam or pressurized liquid) | |
| 01 Peppermint essential oil (active principle) | 5 |
| 02 Gum arabic (active principle thickener and suspender) | 20 |
| 03 Sodium benzoate (antibacterial-antimildew agent) | 0.38 |
| 04 Polysorbate 20 (foaming surfactant) | 6 |
| 05 Polyglycol 300 isostearate (foam thickener) | 4 |
| 06 Purified water | 54.62 |
| 07 Freon 12 (propellant) | 6.5 |
| 08 Freon 114 (propellant) | 3.5 |

Preparation method:

A) The components 03 and 02 are dissolved in 06 in the stated order in a stainless steel dissolving vessel of suitable capacity fitted with a propeller stirrer and turboemulsifier.

B) 04, 05 and finally 01 are added while stirring, and the turboemulsifier is then operated for 15 minutes.

C) Using a metering pump, the suspension is metered in the volume corresponding to the theoretical weight into aerosol cans while stirring.

D) Each can is immediately sealed by clinching the dispenser valve and is then pressurized by means of the propellant, which is fed in under pressure in a suitable quantity by a pumping device.

EXAMPLE 4

| RECTAL FOAM 10% PEPPERMINT | |
|---|---|
| % COMPOSITION (of foam or pressurized liquid) | |
| 01 Peppermint essential oil (active principle) | 10 |
| 02 Gum arabic (active principle thickener and suspender) | 20 |
| 03 Sodium benzoate (antibacterial-antimildew agent) | 0.38 |
| 04 Polysorbate 20 (foaming surfactant) | 10 |
| 05 Polyglycol 300 isostearate (foam thickener) | 4 |
| 06 Purified water | 45.62 |
| 07 Freon 12 (propellant) | 6.5 |
| 08 Freon 114 (propellant) | 3.5 |

Preparation method:

A) The components 03 and 02 are dissolved in 06 in the stated order in a stainless steel dissolving vessel of suitable capacity fitted with a propeller stirrer and turboemulsifier.

B) 04, 05 and finally 01 are added while stirring, and the turboemulsifier is then operated for 15 minutes.

C) Using a metering pump, the suspension is metered in the volume corresponding to the theoretical weight into aerosol cans while stirring.

D) Each can is immediately sealed by clinching the dispenser valve and is then pressurized by means of the propellant, which is fed in under pressure in a suitable quantity by a pumping device.

EXAMPLE 5

| RECTAL FOAM 30% SUCRALFATE | |
|---|---|
| % COMPOSITION (of foam or pressurized liquid) | |
| 01 Sucralfate (active principle) | 30 |
| 02 Xanthan gum (active principle thickener and suspender) | 0.15 |
| 03 Sodium benzoate (antibacterial-antimildew agent) | 0.38 |

-continued

| RECTAL FOAM 30% SUCRALFATE | |
|---|---|
| % COMPOSITION (of foam or pressurized liquid) | |
| 04 Polysorbate 20 (foaming surfactant) | 4 |
| 05 Polyglycol 300 isostearate (foam thickener) | 4 |
| 06 Purified water | 65.62 |
| 07 Freon 12 (propellant) | 6.5 |
| 08 Freon 114 (propellant) | 3.5 |

Preparation method:

A) The components 03 and 02 are dissolved in 06 in the stated order in a stainless steel dissolving vessel of suitable capacity fitted with a propeller stirrer and turboemulsifier.

B) 04, 05 and finally 01 are added while stirring, and the turboemulsifier is then operated for 15 minutes.

C) Using a metering pump, the suspension is metered in the volume corresponding to the theoretical weight into aerosol cans while stirring.

D) Each can is immediately sealed by clinching the dispenser valve and is then pressurized by means of the propellant, which is fed in under pressure in a suitable quantity by a pumping device.

EXAMPLE 6

| RECTAL FOAM 0.02% BUDESONIDE | |
|---|---|
| % COMPOSITION (of foam or pressurized liquid) | |
| 01 Budesonide (active principle) | 0.02 |
| 02 Methyl-p-hydroxybenzoate (bacteriostatic) | 0.12 |
| 03 Propyl-p-hydroxybenzoate (bacteriostatic) | 0.03 |
| 04 Polysorbate 20 (foaming surfactant) | 4 |
| 05 Polyglycol 300 isostearate (foam thickener) | 4 |
| 06 Propyleneglycol | 5 |
| 07 Purified water | 76.83 |
| 08 Freon 12 (propellant) | 6.5 |
| 09 Freon 114 (propellant) | 3.5 |

Preparation method:

A) The components 01, 02 and 03 are dissolved in 07 in the stated order in a stainless steel dissolving vessel of suitable capacity fitted with a propeller stirrer and turboemulsifier.

B) 04, 05, 06 and finally 01 are added while stirring, and the turboemulsifier is then operated for 15 minutes.

C) Using a metering pump, the suspension is metered in the volume corresponding to the theoretical weight into aerosol cans while stirring.

D) Each can is immediately sealed by clinching the dispenser valve and is then pressurized by means of the propellant, which is fed in under pressure in a suitable quantity by a pumping device.

In general, according to the present invention it has been experimentally found that the pharmaceutical compositions of the invention possess a surprising retrograde diffusion capacity.

For example, a 5-ASA composition according to the invention possesses retrograde diffusion tendentially greater than that of a mesalazine enema, while having the ability to adhere for a prolonged time to the intestinal mucosa, and is also able to diffuse homogeneously along the colon, this property not being possessed to the same extent by the enema.

According to the present invention, six male patients suffering from ulcerous coliris in active or remissive form were selected for a clinical trial.

The retrograde diffusion and persistence were evaluated by labelling the preparations under study (4 g of the composition according to the invention, 4 g of enema) with colloidal $^{99m}$Tc sulphide and taking scintiscans at 5, 30, 80, 120 and 240 minutes from administration.

A late scintiscan at 8 and 20 hours was taken in the case of two patients.

The trial was in the form of a crossover study in the sense that each patient was subjected to a scintiscan of the abdomen both after administration of the labelled composition of the invention and after administration of the labelled enema.

The tests, effected three days from each other, were conducted in random order.

RESULTS

| | | Maximum retrograde diffusion | |
|---|---|---|---|
| Patient No. | Disease activity | Composition of invention | Edema |
| 1 | moderate | ascending | transverse |
| 2 | slight | transverse | transverse |
| 3 | remission | descending | descending |
| 4 | remission | sigma | sigma |
| 5 | remission | descending | sigma |
| 6 | moderate | ascending | ascending |

From these results it surprisingly emerges that the composition of the invention has very high retrodiffusion.

This extension is comparable to and even better than that of enemas with 100 ml of solution.

This ability to diffuse is associated with an elevated and prolonged capacity to adhere to the intestinal walls, this adhesion being maintained even after repeated intestinal evacuations by the patent.

We claim:

1. A pharmaceutical composition for the rectal administration of active ingredients which exhibit a topical medication action at the colon level comprising said active ingredients in a liquid vehicle, at least one surfactant, a foaming propellant, and an adjuvant for said active ingredients which is a suspending or solubilizing agent wherein, said active ingredients are formulated in a liquid vehicle able to generate a foam on rectal administration and the foam is contained in a can.

2. A pharmaceutical composition as claimed in claim 1, characterized in that said active ingredient is selected from the group consisting of antiinfectives antibiotics, antiinflammatories antiphlogistics, antispastics, antimeteorics, prokinetics and laxatives.

3. A pharmaceutical composition as claimed in claim 1, characterized in that said active ingredient is chosen from the group consisting of mesalazine, peppermint, sucralfate and budesonide.

4. A pharmaceutical composition as claimed in claim 1, characterized in that said active ingredient is contained in said composition in a concentration range of from about 5 to 50% by weight of the composition.

5. A pharmaceutical composition as claimed in claim 1, wherein the volume of foam developed on administering unit dose of said composition is not less than 100 ml.

6. A pharmaceutical composition as claimed in claim 1 which also comprises a foam thickening amount of a foam thickener.

7. A pharmaceutical composition as claimed in claim 1, which comprises mesalazine, xantan gum, potassium metabisulphite, EDTA bisodium salt, sodium benzoate,

8. A pharmaceutical composition as claimed in claim 1, which comprises peppermint, gum arabic, sodium benzoate, polysorbate, polyglycol isostearate, purified water and freon.

9. A pharmaceutical composition as claimed in claim 1, which comprises sucralfate, xanthan gum, sodium benzoate, polysorbate, polyglycol isostearate, purified water and freon.

10. A pharmaceutical composition as claimed in claim 1, which comprises budesonide, methyl-p-hydroxybenzoate, propyl-p-hydroxy-benzoate, polysorbate, polyglycol isostearate, propylene glycol, purified water and freon.

11. A method of administering a pharmaceutical composition to a patient's distal colon, said method comprising applying to the rectum an active principle which exhibits a prevalently topical medication action in the colon in a sufficient amount of a fluid vehicle which is able to generate a foam which spreads to the distal colon after rectal administration.

* * * * *